United States Patent
Ferrer

(10) Patent No.: US 9,801,695 B2
(45) Date of Patent: Oct. 31, 2017

(54) DENTAL TOOL FOR FORMING A CONTACT AREA ON DENTAL MATRIX

(71) Applicant: Euler R Ferrer, Eastvale, CA (US)

(72) Inventor: Euler R Ferrer, Eastvale, CA (US)

( * ) Notice: Subject to any disclaimer, the term of this patent is extended or adjusted under 35 U.S.C. 154(b) by 0 days.

(21) Appl. No.: 14/846,763

(22) Filed: Sep. 5, 2015

(65) Prior Publication Data

US 2017/0065371 A1 Mar. 9, 2017

(51) Int. Cl.
*A61C 3/00* (2006.01)
*A61C 5/85* (2017.01)

(52) U.S. Cl.
CPC . *A61C 3/00* (2013.01); *A61C 5/85* (2017.02)

(58) Field of Classification Search
CPC ......... A61C 5/125; A61C 8/0089; A61C 3/00; A61C 8/00; A61B 17/282
USPC .............................. 433/4, 153, 156, 157, 159
See application file for complete search history.

(56) References Cited

U.S. PATENT DOCUMENTS

| | | | | |
|---|---|---|---|---|
| 1,304,720 A * | 5/1919 | Young | ...................... | A61C 7/04 433/4 |
| 4,070,745 A * | 1/1978 | Schimmelman | ..... | A41H 37/006 29/268 |
| 5,011,491 A * | 4/1991 | Boenko | .................... | A61F 2/203 606/207 |
| 5,084,935 A * | 2/1992 | Kalthoff | .................... | A61C 7/04 140/106 |
| 5,197,879 A * | 3/1993 | Fowler, III | ............... | A61C 7/02 433/159 |
| 5,197,880 A * | 3/1993 | Lovaas | .................. | A61O 5/023 433/102 |
| 5,368,481 A * | 11/1994 | Hill | ........................ | A61C 13/20 433/159 |
| 6,210,161 B1 * | 4/2001 | Montgomery | ........... | A61C 3/14 433/146 |
| 6,293,790 B1 * | 9/2001 | Hilliard | .................... | A61C 7/04 101/3.1 |
| 6,814,574 B2 * | 11/2004 | Abolfathi | ................. | A61C 7/04 433/159 |
| 2004/0142303 A1 * | 7/2004 | Dryer | ....................... | A61C 3/00 433/153 |
| 2011/0171597 A1 * | 7/2011 | Ahmed | .................. | A61O 5/125 433/156 |

* cited by examiner

*Primary Examiner* — Nicholas Lucchesi
(74) *Attorney, Agent, or Firm* — Kirk A. Buhler; Buhler & Associates

(57) ABSTRACT

A tool for forming a hump along a substantially flat surface of a dental matrix, Said tool having first and second forming surfaces for urged together to form said hump on said matrix inserted therebetween, said forming surface having one portion part-spherical and another transverse convex arch-shaped project and a flat forming surface extending around of said project, and said second forming surface having one portion part-circular and another transverse concave arch-shaped cavity opposite said project.

20 Claims, 3 Drawing Sheets

DENTAL TOOL FOR FORMING A CONTACT AREA ON DENTAL MATRIX

FIELD OF THE INVENTION

The present invention relates to dental pliers and more particularly but not exclusively to pliers for forming the anatomical contour of a contact area on dental matrix.

BACKGROUND OF THE INVENTION

This present invention relates in general to pliers for forming an anatomical contour of the contact area on dental matrix which is used in conjunction with dental restoration techniques.

The treatment of interproximal cavities requires the dental practitioner to remove decayed enamel and dentin along the side or interproximal wall of a tooth which is nested adjacent, and often contacts, healthy teeth. In general, a matrix band is placed around the tooth in order to confine the filling materials to the removed portion of the tooth which is to be filled. At this point, an anatomical contour of the contact area is normally shaped to match the tooth contour.

In the past, the pre-formed convex sectional matrix need the use of dental separator ring to stabilize and tighten the dental matrix, unfortunately these at times collapse. The collapse of the matrix band does not allow a proper formation or morphology of the restorative material in the tooth. Other methods are by forming and burnishing a concave surface on a flat circular matrix bands manually by the dental practitioner, which are time consuming and difficult to perform a constant shape.

In view of the above, it would be desirable to replace the method of how to contour the contact area. However, this will require a metal forming tool capable of forming a anatomical contour similar to the morphology of the contact area of a tooth.

Various types of metal forming tools are known. Thus, U.S. Pat. No. 1,304,720 discloses pliers for shaping the band material about the tooth to be fitted. The pliers have a pair of jaws, each of said jaws being formed with a laterally extending clamping beak.

U.S. Pat. No. 978,430 shows a tool for forming dental crowns. The tool comprises a concave jaw and a convex jaw which carry tooth-like dies for shaping a crown to final form.

U.S. Pat. No. 5,513,513 teaches a tool capable of producing a channel In sheet metal with little or no damage to the surface of the material.

U.S. Pat. No. 5,084,935 teaches a multipurpose, pliers-like tool for use in dentistry. Among the many features of the tool are two pairs of complementary male and female corrugating elements, a wire bending arrangement including an elongated groove and an elongated rib receivable in the groove, and a channel which can receive, in part, the free end of the cone.

U.S. Pat. No. 6,814,574 B2 shows a tool for forming and removing bumps on dental repositioning appliance. The tool comprises a pair of handles each with a curved jaw member lying in the same plane as the handle. The handles are subapically and pivotally connected. A dome shaped cylindrical bump forming projection is positioned at the tip of the first jaw. A circular shaped throughbore is situated in the tip of the second jaw.

U.S. Pat. No. 7,258,047 B1 discloses pliers that are ergonomically designed to reduce incidence of muscle fatigue. The tool comprises first and second arms that are pivotally interconnected utilizing an appropriate mechanical fastener. Further, a bearing is generally located between the first and second arms to hinder friction between the first and second arms and facilitate movement of the pliers between open and closed conditions.

U.S. Pat. No. 8,210,845 B1 teaches a tool that provides a hinge that has a pin and a recess which both center the parts and more evenly spread the wear experienced by such parts. The tool comprises of two pieces each with a handle, a jaw, and a hinge portion between the handle and the jaw, with the hinge portion of each pliers part together forming a hinge. The jaws can be provided with a cutting edge.

Finally, U.S. Pat. No. 5,197,880 shows a pliers-like tool in which each jaw is again provided one with crimping forming surface having a convex arch shaped ridge and the second jaw having a concave arch shaped cavity opposite the ridge for crimping a substantially straight endodontic file.

None of the above tools is designed to form a contact area shaped on a dental metal matrix band.

BRIEF SUMMARY OF THE INVENTION

It is an object of the present invention to provide a tool capable of producing an anatomical shaped of the contact area of a tooth on dental metal matrix.

Another object is to provide a tool that can contour an anatomical contact area on a traditional circumferential flat metal dental matrix in its retainer.

A further object of the invention is to provide a method which makes it possible to form a contact area shape on a the metal matrix while causing little or no damage to surface of the material.

Another object of the invention is to provide a method for producing a depression area on a metal matrix while also imparting a desired curvature in the mesial-distal direction and as well in the cervical-occlusion direction.

It is also an object of the invention to provide a method which permits the adjustment of the width and depth of the anatomical shape to be form on the matrix for different teeth sizes Other objects, features, an advantages will become more readily apparent from the ensuing description in conjunction with the accompanying drawings.

BRIEF DESCRIPTION OF THE DRAWINGS

Preferred forms of the present invention will now be described with reference to the accompany drawings in which.

DESCRIPTION OF THE PREFERRED EMBODIMENTS

Figure 1:
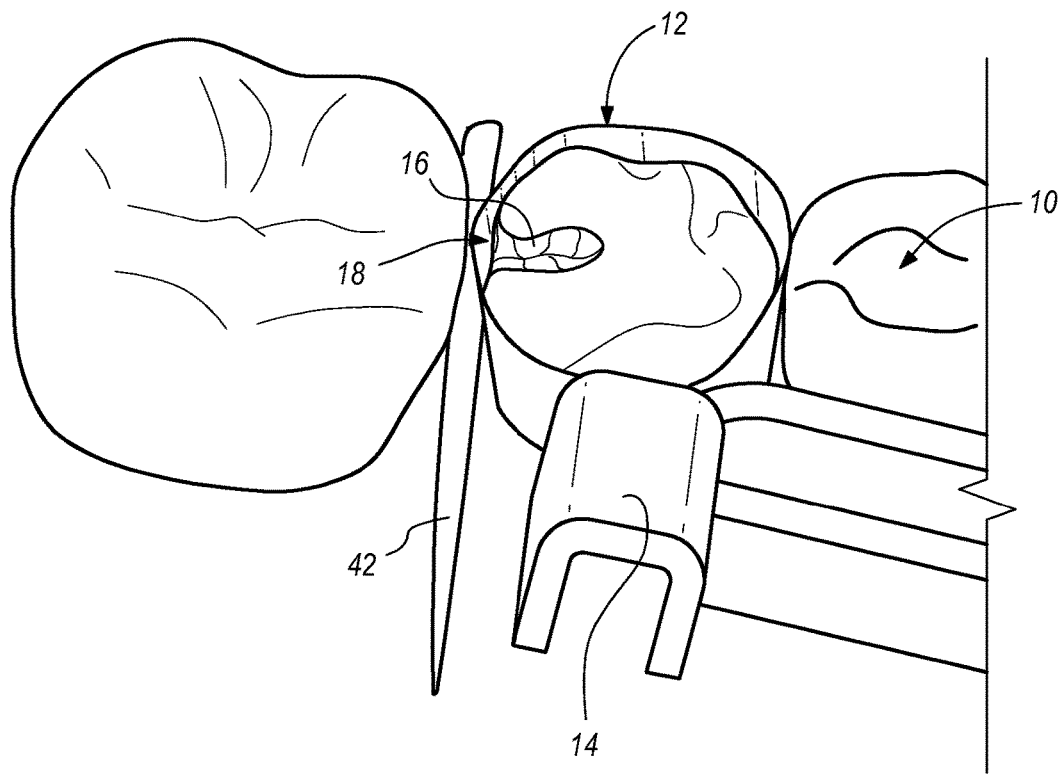
FIG. 1 illustrates a patient's teeth and provides a general indication of how teeth may be restore by the methods and apparatus of the present invention

The present invention provides improved device, system and Methods for treatment of interproximal cavities, where a circumferential flat metal dental matrix is placed around the tooth. Referring now to FIG. 1, a representative of the prepared cavity 16 including teeth 10. The present invention is intended to form an anatomical shape of the contact area 18 from an open cavity 16 to an initial tooth shape which is to be filled. For example, where the circumferential flat metal matrix 12 is placed around the tooth and held by a retainer 14 is relatively flat, a bulbous anatomical contour 18 such of FIG. 5 may desirably be located closer to the adjacent tooth for a proper anatomical contact.

Figure 2A:
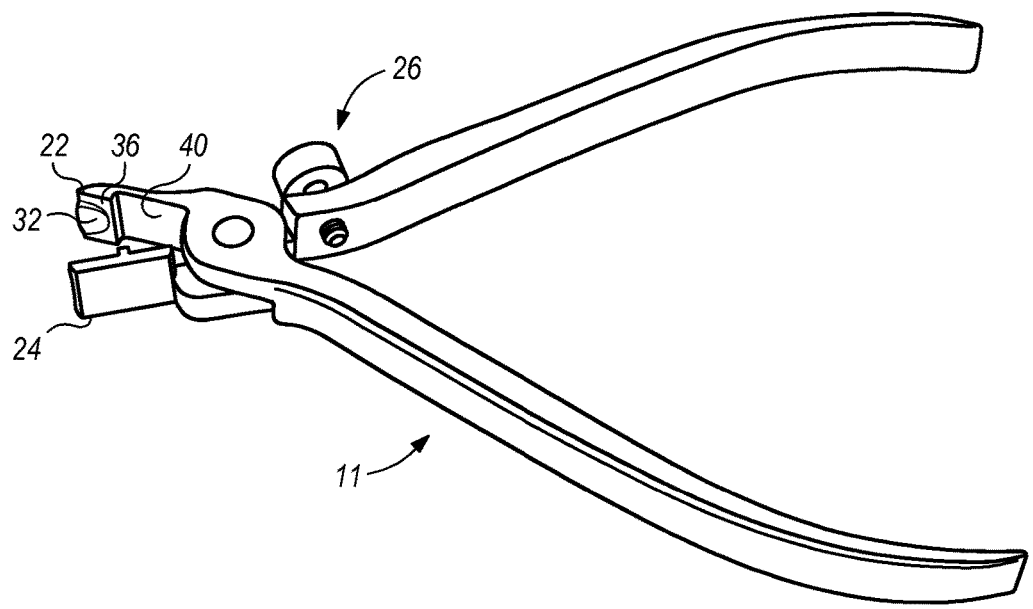
FIGS. 2A and 2B illustrate an exemplary embodiment of dental tool for forming a contour of the contact area onto the dental matrix of FIG. 1.
Figure 2B:
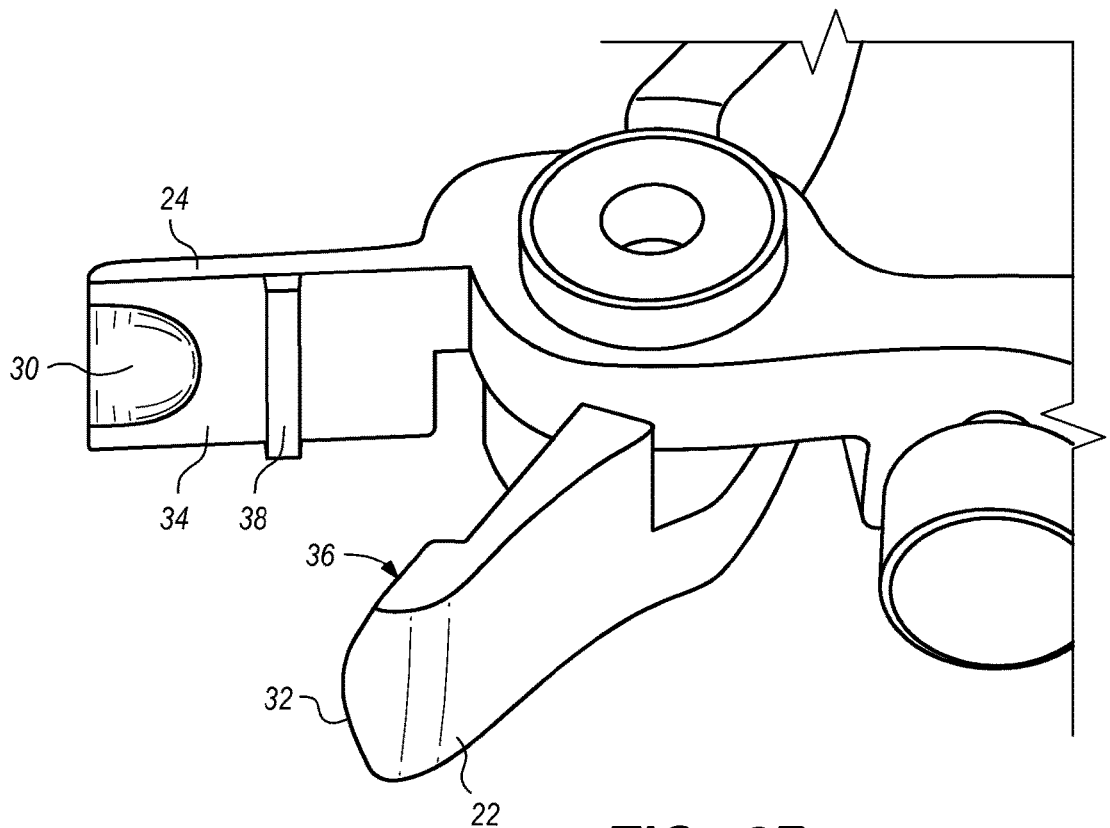

FIGS. 2A and 2B illustrate an exemplary embodiment of dental tool for forming a contour shape of a contact area of a tooth onto a dental matrix 14. The crimping tool 11 having first and second jaws 22 and 24. The crimping tool is similar to pliers with opposing jaws being shaped to achieve the contour area along the dental matrix 12.

The pliers consist of a pair handles each lying in the same plane and pivotally connected. A portion of the first jaw 22 includes a bulbous emulating the contact area of tooth a portion of a partial spherical shape and another transverse convex arched-shaped towards the front end forming project 32 with a flat surface 36 extending around the side of the project and a step down platform 40 where the step up ridge 38 nests. The opposite crimping surface of second jaw 24 portion adapted to receive such bulbous comprises a portion of a partial circular shape and another transverse depression arched-shaped cavity 30 as shown in FIG. 2B with a flat surface 34 extending around the side of the cavity and a step up ridge 38 which receive the bulbous project 32 when the jaws are urged together in the crimping operation as illustrated in FIG. 3.

Figure 3:
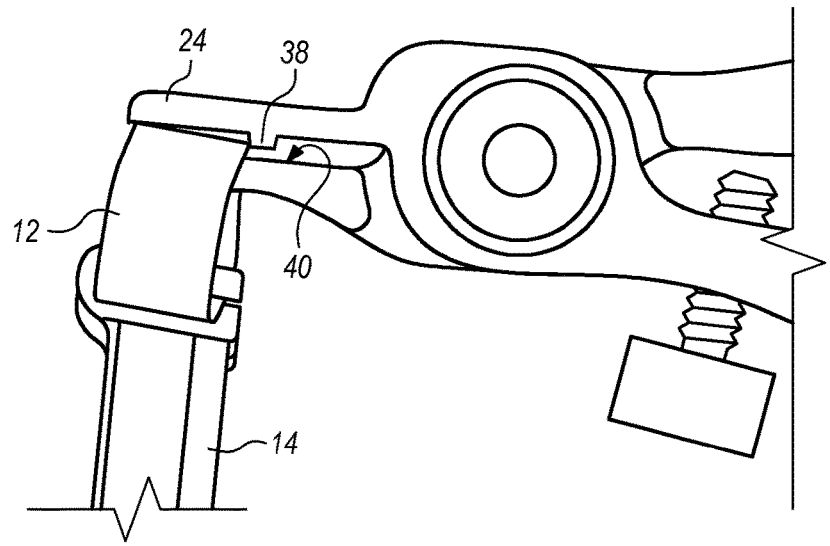
FIG. 3 shows an exemplary application of the tool of FIGS. 2A and 2B onto a dental matrix.
Figure 4:
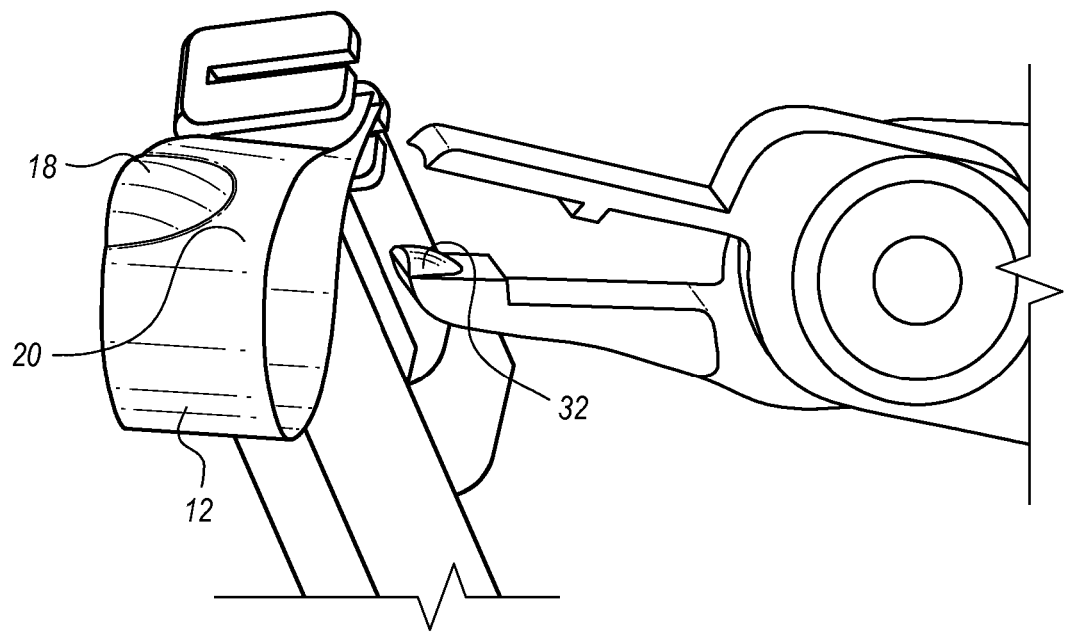
FIG. 4 illustrate a contour area formed on a dental matrix after the application of the dental tool.

To form the contact area shape 18 the matrix band is placed between the jaws as shown in FIG. 3 so that the cervical edge 20 of the band 12 is substantially in contact with the ridge 38 to align the matrix 12 ascertain a proper distance from the cervical floor of the prepared cavity 16. To form a device of the invention as shown in FIG. 4, the user simple insert the portion of a matrix 12 between the open jaws as illustrated in FIG. 3, holding the retainer 14 with one hand, and with the other hand, holding and squeezing the crimping tool handles so the opposite jaws are urged together.

A flat surfaces 36 and 34 surrounding project 32 and cavity 30 are provided as shown in FIGS. 2A and 2B thus the forming operation can be performed rather easily and without bending or damaging the surface of the matrix 12.

Figure 5:
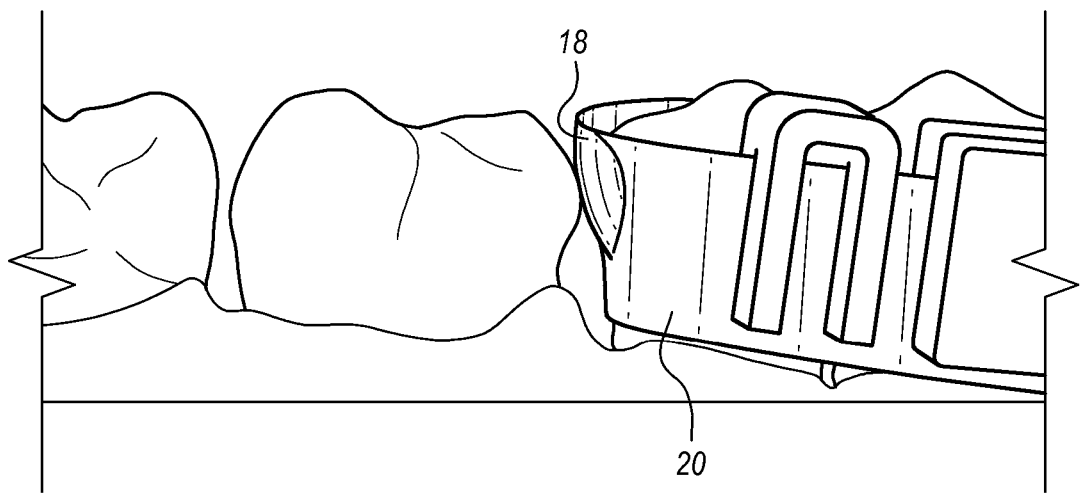
FIG. 5 shows a portion of the dental matrix of the invention in a tooth illustrating the use thereof for cavity restoration.

The traditional circumferential flat metal matrix 12 is shown in FIG. 5 with the anatomical contour shaped 18 for a proper restoration of the contact area and the flat cervical portion 20 to seal the cervical floor of the prepared cavity 16 and to nest the wedge 42 to stabilize said dental matrix 12.

The crimping tool 11 also has an optional thumb screw 26 as shown in FIG. 2A. Turning the thumb screw in and out the user may adjust the depth and width of the anatomical shape 18 to be formed on the matrix for different teeth sizes.

It is to be understood that the length and shape of the working jaws of The dental tool can be designed to fit the task for which the tool is to be used. The parts of the tool are also preferably made of a single piece of metal, usually of stainless steel. The shapes shown herein are readily made on conventional cast method, and can effectively be cleaned and sterilized.

Those skilled in the art will now see that certain modifications can be made to the tool and related methods herein disclosed with respect to the illustrated embodiments, without departing from the spirit of the present invention. And while the invention has been described above with respect to preferred embodiments, it will be understood that the invention is adapted to numerous rearrangements, modifications, and alterations, and all such arrangements, modifications, and alterations, are intended to be within the scope of the appended claims.

What which is claimed:

1. A forming tool for crimping a substantially flat surface of a dental matrix comprising:
   a first jaw member having a first forming element rising from a flat surface and pivotally connected to a second jaw member having a second forming element;
   said first forming element being a bulbous protrusion;
   said second forming element being an arched-shaped cavity;
   said first forming element and said second forming element being movable towards and away from one another between an open position in which said first forming element and said second forming element are spaced from one another and a closed position in which said first forming element and said second forming element contact each other;
   said second forming element further having a planar surface extending from said arched-shaped cavity forming element with a transverse depression which extends in a predetermined direction within said planar surface and is bounded on three sides by said planar surface defining an open cavity profile that extends away from said pivotal connection and extends out a fourth side through a front face of said second jaw member in said arched-shape, and
   said first forming element bulbous protrusion faces said arched-shaped cavity and essentially makes contact with said first forming element in said closed position.

2. The tool of claim 1, wherein said arched-shaped cavity has a first portion that is partial circular shape and a second portion that has a transverse arched-shaped depression that extends away from said pivotal connection.

3. The tool of claim 1, wherein said planar surface has a depression portion that has a part-circular arch and a transverse arch-shape in a plane normal to said planar surface that extends away from said pivotal connection, and wherein said bulbous protrusion is a least part-spherical shape and has a radius substantially equal to said arch.

4. The tool of claim 1, further including a thumb screw on an opposing side of said pivotal connection from said first and second forming elements.

5. The tool of claim 4, wherein said thumb screw limits closure gap from of said first jaw to said second jaw.

6. The tool of claim 1, wherein said second jaw member further includes a step-up ridge that is elevated perpendicular from said planar surface.

7. The tool of claim 6, wherein said first jaw member further includes a step-down platform that is lower than said planar surface.

8. The tool of claim 7, wherein said step up ridge bypasses said step-down platform when said tool is closed position.

9. The tool of claim 6, wherein said step up ridge provides a stop for a dental matrix band.

10. The tool of claim 9, wherein said ridge aligns said dental matrix band in said tool.

11. A tool for forming a hump along a substantially flat surface of a dental matrix comprising:
    said tool having a first and a second forming surface configured for being urged together to form a hump on a dental matrix inserted there between said first and said second forming surfaces;

said first forming surface having a flat forming surface with a part-spherical projection and a convex transverse arched-shaped projection that extends to a front edge of said first forming surface , and said second forming surface having a part-circular shaped and a transverse concave arch-shaped cavity that extends to a front edge of said second forming surface.

12. The tool of claim 11, wherein said first forming surface is received in said second forming surface when said tool is closed.

13. The tool of claim 11, wherein said tool is made from metal.

14. The tool of claim 11, further including a thumb screw on an opposing side of said pivotal connection from said first and second forming elements.

15. The tool of claim 14, wherein said thumb screw limits closure of said first forming surface relative to said second forming surface.

16. The tool of claim 11, wherein said second forming surface further includes a step-up ridge that is elevated from said planar surface.

17. The tool of claim 16, wherein said first forming surface further includes a step-down platform that is lower than said flat forming surface.

18. The tool of claim 17, said step up ridge bypasses said step-down platform when said tool is closed position.

19. The tool of claim 16, wherein said step up ridge provides a stop for a dental matrix band.

20. The tool of claim 19, wherein said ridge aligns said dental matrix band in said tool.

* * * * *